United States Patent [19]
Van Donselaar et al.

[11] Patent Number: 4,930,889
[45] Date of Patent: Jun. 5, 1990

[54] METHOD OF AND INSPECTING APERTURED MASK SHEETS

[75] Inventors: Bastiaan J. Van Donselaar; Willem D. Van Amstel, both of Eindhoven, Netherlands

[73] Assignee: U.S. Philips Corporation, New York, N.Y.

[21] Appl. No.: 220,850

[22] Filed: Jul. 18, 1988

[30] Foreign Application Priority Data

Jul. 22, 1987 [GB] United Kingdom ............... 8717306

[51] Int. Cl.$^5$ ............................................. G01N 21/88
[52] U.S. Cl. ................................. 356/237; 356/384; 356/430; 358/106
[58] Field of Search ............... 356/237, 239, 384, 430; 358/106

[56] References Cited

U.S. PATENT DOCUMENTS

3,918,815 11/1975 Gadbois ............................ 356/384
4,282,511 8/1981 Southgate et al. ................ 356/430
4,454,545 6/1984 Duschl ............................... 358/106

Primary Examiner—Vincent P. McGraw
Assistant Examiner—S. A. Turner
Attorney, Agent, or Firm—John C. Fox

[57] ABSTRACT

An on-line method of and apparatus for inspecting an apertured mask sheet to be formed into a shadow mask for a color cathode ray tube are disclosed. In one of several embodiments described the mask sheet is linearly scanned by a laser spot transverse to the direction of advancement of the mask sheet. The peak values of the grey levels of the laser light transmitted by the mask sheet are detected and the data is convoluted electronically to form a series of convolution windows. The grey levels of the successively formed convolution windows are compared to at least one reference value and an output is produced at least in those cases where an error in the mask aperture size is detected.

31 Claims, 9 Drawing Sheets

METHOD OF AND INSPECTING APERTURED MASK SHEETS

BACKGROUND OF THE INVENTION

The present invention relates to a method of inspecting apertured mask sheets used as shadow masks in colour display tubes.

The apertures in shadow masks are formed by etching metal sheet material such as mild steel sheet. The etching is done chemically after contact-exposure printing using a master pattern etching mask. In order to ensure the correct colour reproduction of an object at the cathodoluminescent screen which comprises triplets of phosphor elements, three electron beams converge at the screen on their respective phosphor elements to produce a multicoloured image. Defects in the shadow mask apertures may give rise to faults in the image, for example, the colour is defective due to the microspot at the screen being significantly wider than a triplet element as a result of the shadow mask aperture being too wide, or the brightness is uneven because the microspots are too small as a result of the aperture being much smaller than specified. If such defects are the result of a processing failure, then corrective action must be taken promptly to avoid too many rejects. Accordingly, it is desirable that the etched shadow mask sheets be inspected on-line. Also, it is desirable that the method of inspection be readily adaptable to the mixture of different sizes of shadow masks which may be produced. The method ought also to be adaptable to different aperture sizes, not only between one size of shadow mask and the next, but also between the centre and edges of any one mask sheet.

From U.S. Pat. No. 4,641,256, a method is known to measure the transmission of energy through the aperture pattern to verify that the shadow masks are suitable for the intended use. The transmission of inspection areas of the shadow mask is measured and compared to transmission limits. If the total transmission or the transmission of any of the inspection areas fails to fall within the transmission limits, the shadowmask can be failed. This method, however, is capable only of indicating the average size of the shadow mask apertures. Other errors, for instance oddly shaped apertures, with substantially "normal" average size, however, go undetected. As the picture quality is increased, the need for improved methods of inspecting apertured mask sheets increases. It is an object of the invention to provide a method of inspecting apertured mask sheets with improved diagnostic capabilities.

SUMMARY OF THE INVENTION

According to the present invention there is provided a method of inspecting an apertured mask sheet, characterized by providing relative movement between an apertured mask sheet and a source of radiant energy along a path of movement; producing, by scanning across the mask sheet in a direction transverse to said path of movement, a grey level signal corresponding to radiant energy passed by apertures in the mask sheet; deriving from the grey level signal a plurality of peak signals which correspond to the maximum transmission of each of the apertures scanned at; and successively comparing the peak signals with at least one reference value to determine whether the transmission of each aperture scanned is acceptable.

The method in accordance with the present invention is based on the recognition of the fact that a relatively low resolution spot of radiation can be used to obtain rapidly a relatively accurate measurement of the mask transmission. In order to be able to inspect an apertured mask sheet on-line in a time period of the order of 4 seconds, the data processing has to be streamlined. Convoluting the data to be processed at an early stage enables this objective to be fulfilled.

In one embodiment of the present invention the shadow mask sheet is linearily scanned with a spot of radiant energy, for example laser light, which spot is of a picture element (pixel) size, the area of the spot being a predetermined fraction of the nominal area of an aperture in the mask sheet. In this embodiment the grey levels of successive pixel sized areas are detected, digitised and stored. Thereafter the convoluted data is produced by electronically combining the already stored grey levels of successive predetermined arrays of pixels, each said array being shifted by one pixel from a preceding array so that the preceding array is partially overlapped by the next following array and so on. In order to be able to inspect different sizes of mask sheets at will, the method is adaptable so that the number of pixels in an array can be varied electronically. Also by examining simultaneously the grey levels of two or more differently shaped arrays of pixels, a mask sheet can be inspected for different faults. The reference value against which the convoluted data is compared may be formed by averaging the peak values of a predetermined number of convoluted data. Obtaining a reference value this way enables the inspection method to be adaptive to mask sheets in which the aperture widths are graded between the centre and the edges.

In a second embodiment of the present invention the convolution of the data is carried out by the beam of radiant energy producing a spot having a size greater than that of an aperture in the mask sheet, the detected grey level comprising the convoluted data. Such an embodiment enables the hardware of the signal processing system to be simplied but this is at the expense of flexibility in adapting the spot size to suit different mask sizes. The size of the spot should be such that it has a length corresponding to the length of a mask aperture plus the height of a bridge between successive apertures and a width greater than the width of the designated maximum width of an aperture. The detection of the grey level of the spot is determined by digitising the analogue grey level signal at a succession of time intervals, each time interval corresponding to a sub-multiple of the time of travel of the spot across one aperture of the shadow mask.

In a third embodiment of the invention the spot of radiant energy is of elongate shape, for example having a length corresponding to the nominal length of an aperture plus the length of a bridge between successive apertures and a width corresponding to a submultiple of the width of an aperture, so that a partial convolution of the grey level signal is done optically and a further partial convolution can be effected electronically.

A bigger scanning spot has the advantage over a smaller one of not requiring such stringent requirements of the mechanical parts of the apparatus. Additionally, by dividing the succession of peak signals into odd-numbered and even-numbered sub-sequences and comparing the peak values in each sub-sequence with its respective reference value, the method is accurate even though the spot size may exceed a specified minimum size.

The present invention also provides an apparatus for inspecting an apertured mask sheet, comprising radiant energy producing means and radiant energy detecting means for detecting the amount (or grey level) of radiant energy passed by the mask sheet disposed on opposite sides of a path of relative movement of the mask sheet, said producing means and detecting means being so constructed and operated that a linear scan, transverse to said path of movement, can be effected, means for deriving a succession of peak signals from the detected grey levels, and comparing means for comparing each peak signal with at least one reference value.

BRIEF DESCRIPTION OF THE DRAWINGS

The present invention will now be described, by way of example, with reference to the accompanying drawings, wherein.

In the drawings the same reference numerals have been used to indicate corresponding parts.

DESCRIPTION OF THE PREFERRED EMBODIMENTS

Figure 1:
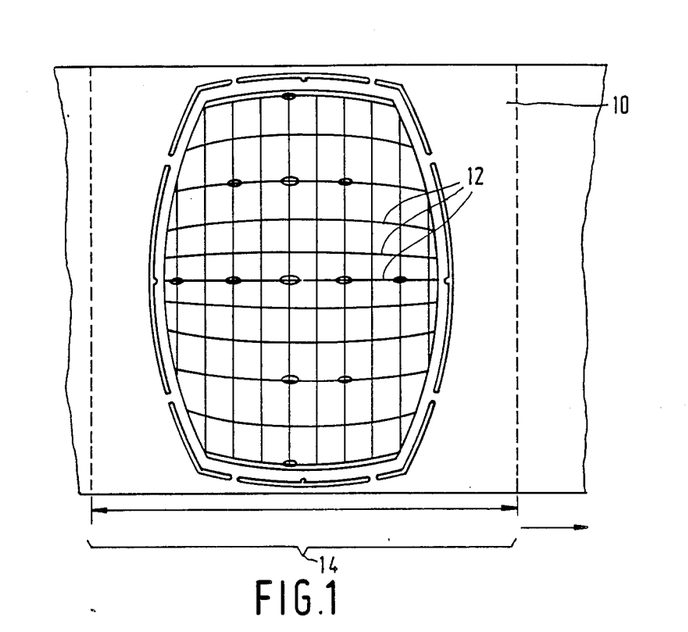
FIG. 1 is an elevational view of a mask sheet.

Shadow masks are produced by etching a predetermined pattern of apertures in, for example, a mild steel sheet. The pattern of apertures is produced on the steel sheet by contact-exposure printing in an applied photoresist using a master pattern. The etching process is well-known in the art and accordingly it will not be described in the present specification. However in order to facilitate an understanding of the present invention it is necessary to realise that the shadow masks are produced from rolls of strip metal 10 (FIG. 1). Mixtures of different sizes of shadow masks, for example 14", 16", 20", 22", 26" and 27", are produced on a substantially continuous basis. The aperture sizes in a mask depend on the size of the shadow mask and also on the intended mask transmission, which may require the apertures at the central region to be wider or of greater area than at the edges, particularly the east-west edges. Also the apertures, which are elongate, are normally arranged so that they lie in generally north-south extending columns 12, which are straight at the centre but concave at the edges with respect to the centre.

In the actual etching of the mask sheet, the strip metal is advanced slowly and continuously. The feed rate of the strip metal is linked to the processing time of the largest anticipated size of a shadow mask, which may take up to 4 seconds to pass a fixed point on the production line. Consequently, an on-line inspection system must be capable of completing its inspection of a shadow mask sized section 14 (FIG. 1) of the etched strip metal within say four seconds, must be adaptable to different sizes of shadow mask and must cope with apertures in any one mask sheet not being of the same size and not being parallel to each other.

Figure 2:
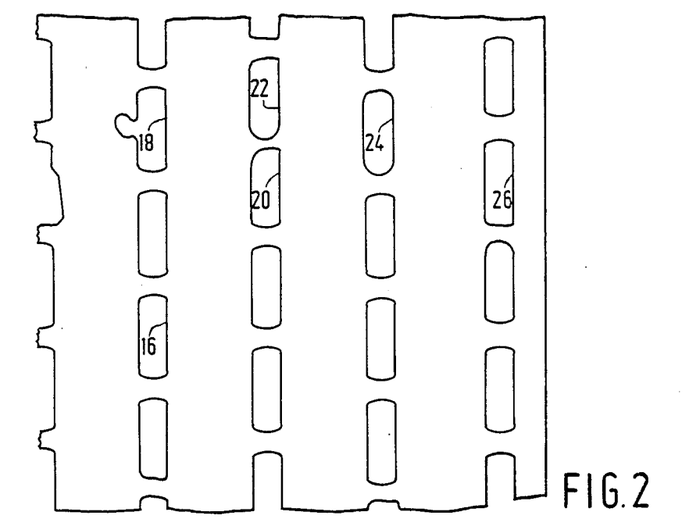
FIG. 2 is an elevational view of a portion of a mask sheet illustrating a number of defective apertures.

FIG. 2 shows a portion of an etched shadow mask sheet and illustrates a number of faults which can occur in the etching of the mask sheet, which mask sheet if used as a shadow mask in a colour cathode ray tube may give rise to unwanted local variations in the colour and brightness of an image being reproduced. If it is assumed that aperture 16 is an acceptable aperture shape then by comparing the shape of this aperture 16 with the shapes of the apertures 18, 20, 22, 24 and 26 the differences between them will be readily apparent. There are many reasons for the defects in these apertures 18 to 26, one of the more readily identifiable being that the shadow mask master pattern has become defective. Accordingly it is desirable to be able to check every aperture of a shadow mask on-line so that defects can be detected quickly and a remedy found, for example, replacement of the shadow mask master pattern.

In order to implement the method in accordance with the present invention, the mask sheet 10 is inspected as it is transported continuously through an inspection station during a time period of, say four seconds.

Figure 3:
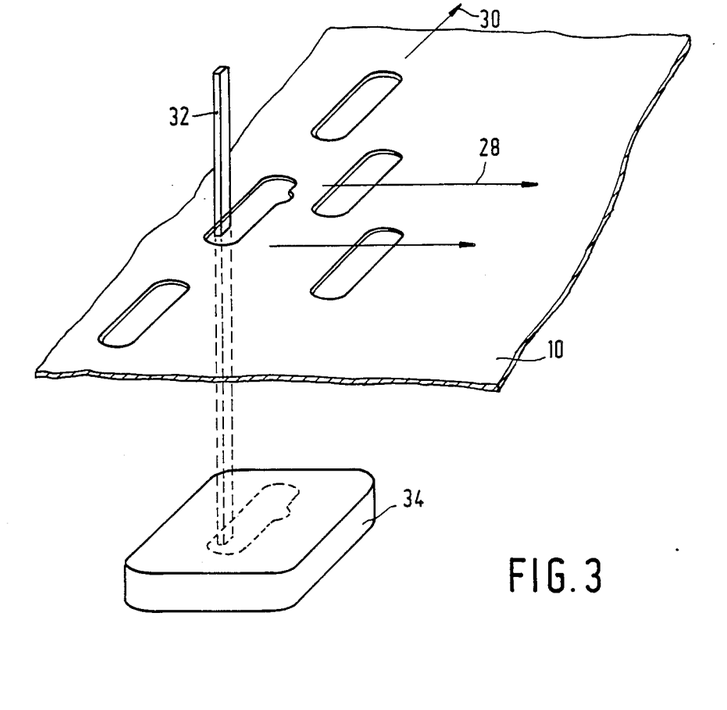
FIG. 3 illustrates diagrammatically the scanning of a mask sheet with a picture element size spot.

In a first embodiment, shown in FIG. 3, the mask sheet 10 is linearly and rapidly scanned in a direction 28, which is substantially orthogonal to the sheet feed direction 30, by means of a beam 32 of radiant energy. The beam 32 can be produced by a laser, but other forms of light beams may be used. The spot 32a (FIG. 4) has the size of a picture element (or pixel) which in this embodiment is a sub-multiple of a mask aperture, say 130 μm square. The radiant energy transmitted by the apertures in the mask sheet is directed by an optical system (not shown) onto a detector 34 disposed on the opposite side of the path of movement of the metal sheet 10. For convenience of description, the amount of light transmitted will be referred to as its grey value. When the light beam 32 passes over an opaque portion of the mask sheet the detector 34 will produce a low grey value and when the light beam passes through an aperture it will have a high grey value. Assuming that the mask sheet has been etched correctly, as the light beam 32 scans across the mask sheet 10 the detected signal will vary cyclically between a low grey value and a predetermined high grey value. However if an aperture is of too great an area, such as the apertures 18 and 24 in FIG. 2, then the cyclic variation will not be followed.

In order to simplify the processing of the grey values, the data is convoluted and it is the convoluted data which is processed.

Figure 4:
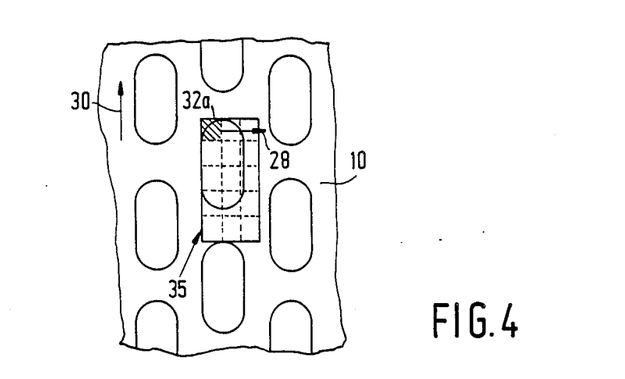
FIG. 4 illustrates a portion of a mask sheet and an electronically produced 3×5 pixel convolution window.

FIG. 4 shows the light spot 32a scanning the mask sheet 10. This Figure also shows a convolution window 35 whose area is 3 picture elements (or pixels) wide by 5 picture elements long. In the first embodiment of the method, the detector 34 detects the grey levels of the pixels in successive time intervals, each time interval corresponding to a submultiple of the time of travel of the spot 32a across one aperture of the shadow mask. The next successive line scan corresponds to a relative shift of the mask sheet by one pixel in the feed direction 30. The grey levels of the pixels are stored and the grey level of convolution window 35 each time comprises the sum of the grey levels of the pixels forming the convolution window 35. The convolution window 35 effectively moves at the scanning speed of spot 32a. This can be done electronically as will now be described.

Figure 5:
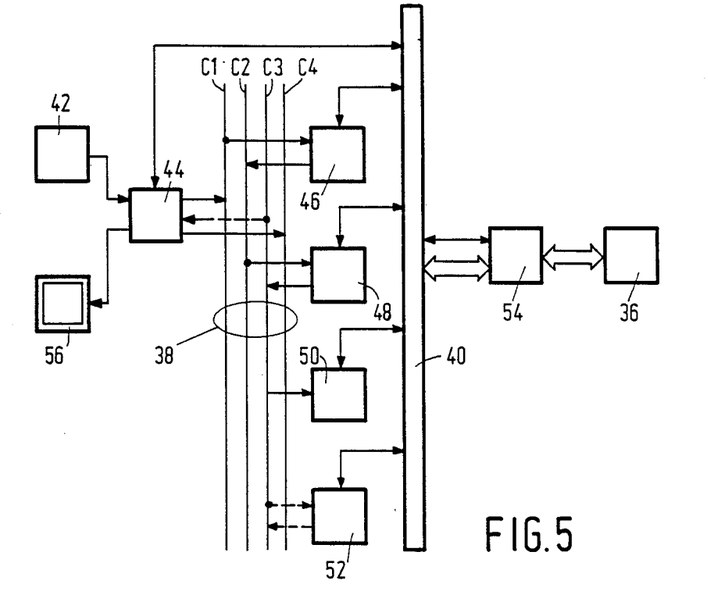
FIG. 5 is a block schematic diagram of an embodiment of a signal processing system for implementing the method in accordance with the present invention.

FIG. 5 is a block schematic diagram of a picture acquisition and processing system which is used in conjunction with a general purpose computer 36. The system is of a flexible type comprising a number of general purpose circuit boards 44 to 52 connected between a picture bus 38 formed by three parallel channels C1, C2 and C3, each 8 bits wide, for the interconnection of digitised picture signals, and a fourth channel C4 for control signals such as clock, picture enable, line enable, etc., and a general purpose instrumentation bus 40.

More particularly the system includes a laser scanner 42 which has an output connected to a linear array and laser scanning acquisition unit (LAU) 44. The analogue picture signal from the laser scanner 42 is digitised in the LAU 44 and transmitted on channel C1. A convolution card (CVC) 46 which processes the grey level signals, has a signal input connected to the channel C1 and produces a convolution result which is applied to the channel C2. An error detection card (EDC) 48, which checks for errors in the convoluted signal, has a signal input connected to channel C2 and a signal output connected to the channel C3 which carries the error reports. A picture transfer buffer (PTB) 50 has a signal input connected to the channel C3. The PTB 50 stores the error reports with their coordinates in a buffer. The computer 36 has access to these error reports, and, via bus converter 54, can process them in software. Optionally an image frame store (IFS) 52 can be provided having a signal input and a signal output which can be connected to a selected one of the channels C1 to C3. The data stored in the IFS 52 can be displayed via a display part 56. The IFS 52 is primarily useful in testing the system because each step in the data processing can be made visible, but it can also be useful in storing data relating to the overall transmission of the mask sheet.

The operation of the apparatus depicted in FIG. 5 will now be described briefly. The laser scanner 42 linearly scans the shadow mask sheet with the beam 32 (FIG. 3). The analogue value of the varying grey level signal produced is detected and transferred to the LAU 44 which digitises the analogue value and in response to control signals, transfers the digitised data onto channel C1 of the picture bus 38. The CVC 46 accepts the data which is then convoluted by forming an electronic convolution window. The output from the CVC 46 comprises a series of peaks. These peak signals are transferred to the EDC 48 via the channel C2. In the EDC 48 several (4 8, 16 or 32) of the previous peaks signals are averaged and the average is used as a reference against which the newly received peak signal is compared. A deviation in signal value of more than say ±15% in relation to the average value is detected and is reported as a fault in the etched masked sheet. The averaging of several previous peaks enables the EDC 48 to adapt to situations where the area or width of the apertures is intentionally different to obtain a desired mask transmission. The error reports from EDC 48 are transferred on the channel C3 to the PTB 50. The stored error reports can be transferred via the bus converter 54 to the computer 36 for analysis.

Figure 6:
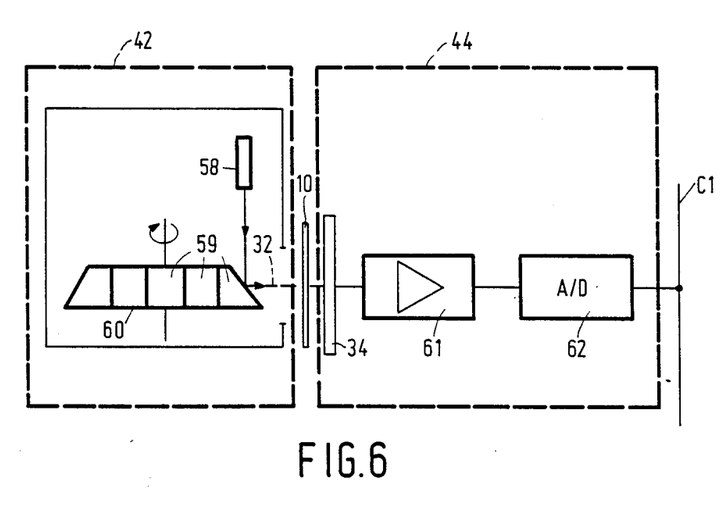
FIG. 6 is a diagrammatic view of the laser scanner and laser scanning acquisition unit of FIG. 5.

FIG. 6 shows the laser scanner 42 and the LAU 44. The laser scanner 42 is designed to allow the sheet metal 10 to be transported vertically between a scanning laser light source and the detector 34. The scanning laser light source comprises a laser 58, the light from which is directed onto reflecting facets 59 of a rotatable prism 60. The inclination of the facets 59 is such that the path of movement of the light reflected by the lens facets is substantially the same but as the mask sheet is continuously moving slowly contiguous line scanning of the mask sheet results.

The analogue grey level signal detected by the detector 34 of the LAU 44 is amplified using a computer controlled amplifier 61 so that it is suitable to make optimal use of an analogue-to-digital (A/D) converter 62. In the (A/D) converter 62 the analogue grey level signal is digitised into a series of 8 bit signals and these digital signals are applied together with control signals to the channel C1.

Figure 7:
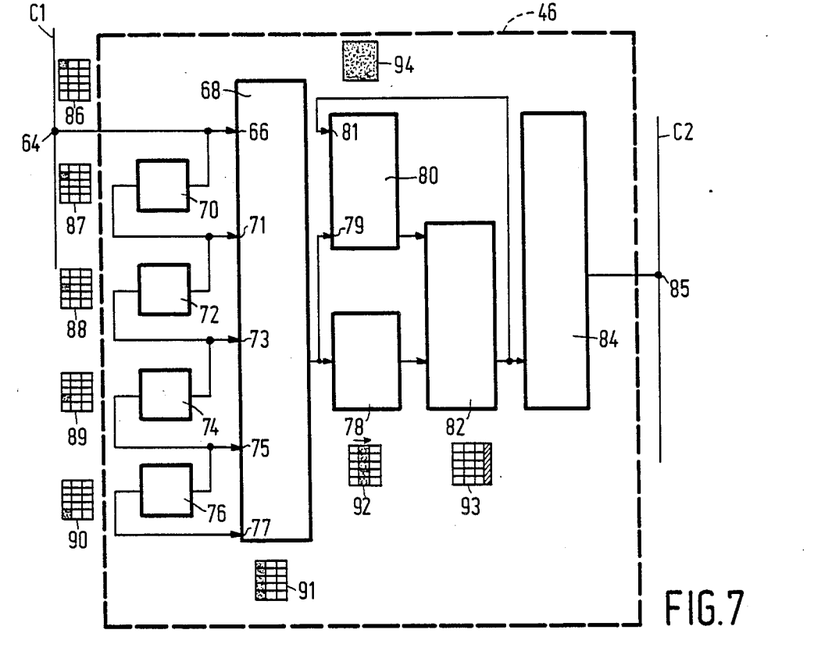
FIG. 7 is a block schematic diagram of a convolution card of FIG. 5.

FIG. 7 is a block schematic diagram of the convolution card 46. For convenience of description it will be assumed that the digitised grey level signals from the LAU 44 are convoluted to a window 3 pixels wide and 5 pixels high. However it is to be understood that several convolution cards can be provided, each capable of producing a different size of convolution window to suit different shadow mask aperture sizes and, if required, to produce simultaneously two or more convolution windows of different sizes which can be used for the detection of different defects in the etched shadow mask sheets. The convolution card 46 comprises a data input terminal 64 which is connected to a first data input 66 of a column adder 68. Four line stores 70, 72, 74 and 76 are connected in series between the data input 64 and an input 77 to the column adder 68. The line stores 70 to 76 comprise shift registers which are clocked at the pixel rate. The outputs of the line stores 70, 72 and 74 are connected to respective inputs 71, 73 and 75 of the column adder 68. An output of the column adder 68 is connected to a column shifter 78 and to a first input 79 of an area adder 80. Outputs of the column shifter 78 and the area adder 80 are connected to respective inputs of an end column substractor 82. An output of the subtractor is connected to a second input 81 of the area adder 80 and also to an input of a result and normalization block 84 which is connected to an output terminal 85.

In operation, assuming that the convolution window is 3 pixels wide and 5 pixels high, then the required data is stored by feeding-in the digitised grey level signals produced as the laser scanner 42 scans repeatedly across the mask sheet. The rate of storage is related to the time the beam 32 (FIG. 3) takes to travel the distance constituted by one pixel. In the case of the first linear scan by the beam 32 the grey values are applied in sequence to the input 66 of the column adder 68 and also to the line store 70. At the commencement of the second linear scan by the beam 32, the data relating to the second scan is applied to the input 66 and to the line store 70 while simultaneously the data relating to the first line is read out from the line store 70 and is applied to the input 71 of the column adder 68 and to the line store 72. This cycle is repeated twice more so that at the end of the fourth line scan, the line stores 70, 72, 74 and 76 are full, with the oldest information being held in the store 76 and the most recently detected signals being held in the store 70. At the arrival of the first grey level value for the fifth line, the first pixel values relating to the first four lines are present at the inputs 77, 75, 73 and 71 of the column adder 68. This situation is shown in the pictograms 86 to 90. The column adder 68 sums the five grey level signals, pictogram 91, and the sum is applied simultaneously to the column shifter 78 and to the area adder 80 via the input 79. At the occurrence of the next clock signal the sum of the second pixel values on the inputs 66, 71, 73, 75 and 77 are added and the sum signal is again applied simultaneously to the column shifter 78 and the area adder 80. In the column shifter the first sum signal is shifted one column position to provide space for the storage of the second sum signal, see pictogram 92. The cycle repeats for the third pixel values so that the area adder stores the accumulated grey values of the 3×5 convolution window pictogram 94. During the next clock period the convoluted data is normalised to eight bits in the block 84 and applied to the output terminal 85, the column shifter 78 shifts the longest held column sum signal into the end column subtractor 82, pictogram 93, and the area adder stores the sum of the first four column signals, which signal is also applied to the subtractor 82 in which the area sum signal is adjusted by the subtraction of the longest held column sum signal, and the difference, which represents the area sum of columns 2 to 4, is applied to the input 81 of the area adder and also to the result and normalisation block 84. This signal is then applied to the output terminal 85.

Figure 8:
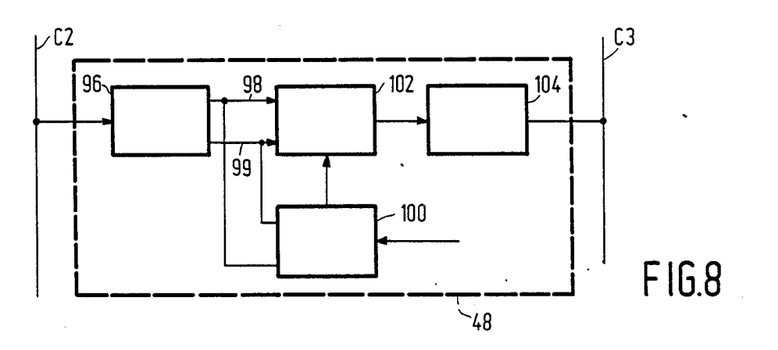
FIG. 8 is a block schematic diagram of an error detection card of FIG. 5.
Figure 9:
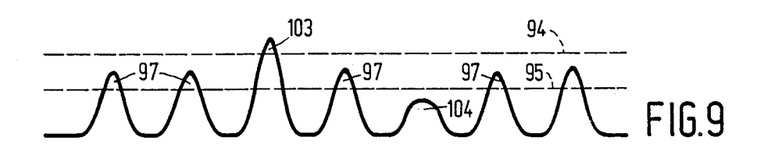
FIG. 9 is a graph which illustrates the error detection principle of the error detection card shown in FIG. 8, FIGS. 10, 11 and 12A to 12C illustrate diagrammatically a simplified numerical example of the method in accordance with the present invention.

FIG. 8 is a block schematic diagram of the error detection card 48. As mentioned previously if a mask sheet has been etched correctly then the convoluted data will systematically vary between a minimum value and a maximum (or peak) value. If an aperture in the mask sheet is defective then this can manifest itself by the peak value being too low or too high than a reference peak value and/or the peak value occurring at the wrong instant relative to the other peak values. Accordingly the card 48 is arranged to check to see if the peak values lie between upper and lower threshold values 94, 95 (FIG. 9) which threshold values can be made adaptive on the basis that the reference value is an average of the preceding 4, 8, 16 or 32 peak values. By making the system adaptive in this way it is able to be used with mask sheets in which the aperture sizes are deliberately varied to obtain a predetermined mask transmission.

The error detection card 48 comprises a peak detector 96 connected to channel C2. The peak detector 96 selects the amplitudes of the successively occurring peaks 97 (FIG. 9) and the time of their occurrences which provide respective outputs 98, 99 from the peak detector 96. These outputs are applied to an average area function detector 100 which calculates the upper and lower threshold values 94, 95 (FIG. 9) and supplies these values to an error threshold detector 102 which compares the peaks 97 with the threshold values. In the event of a peak, such as the peak 103 or 104, having an amplitude which is too great or too small then this is regarded as indicating a fault in the shadow mask sheet 10 and an error signal together with information relating to the position of the error is produced by an eror detector circuit 104 and is supplied to an output connected to the channel C3.

Reverting to FIG. 5, the functions of, and information provided by, the picture transfer buffer, PTB, 50 comprise the buffering of direct picture data in pixels or the results of processing in the EDC 48. This data is supplied to the computer 36 which can process it in software.

The computer 36, which may comprise a Microvax, M68000 (Philips) or a P890 (Philips), processes the data from the PTB 50 so that it consists of grouping of individual error indications belonging to the same error, the display of a list of detected errors with their coordinates and weights for each error.

Figure 10:
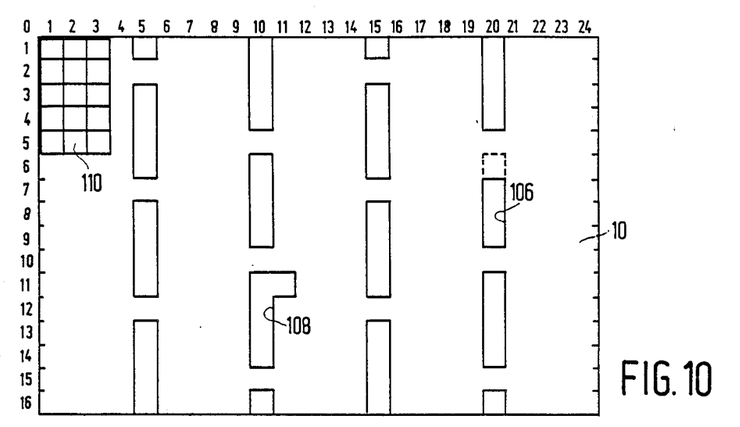
Figure 11:
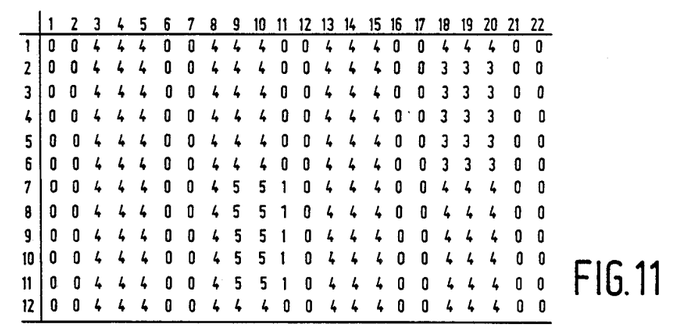
Figure 12A:
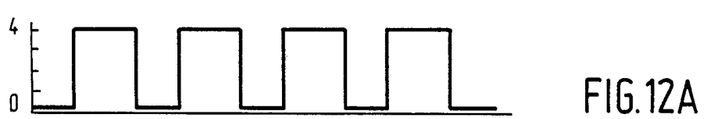
Figure 12B:
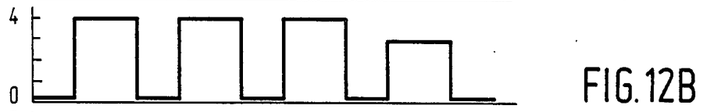
Figure 12C:
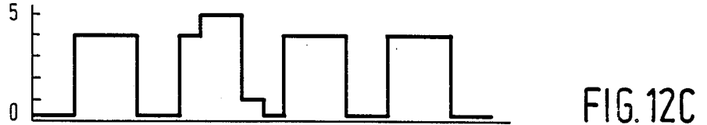

In order to provide a simplified numerical example of the method in accordance with the present invention, FIG. 10 illustrates a shadow mask sheet 10 having two defective apertures 106 and 108 and the remainder being normal, that is 1 pixel wide and 4 pixels long. The electronic convolution window 110 is illustrated in the top left hand corner, and the horizontal and vertical pixel positions are enumerated taking the top left-hand corner as the origin O. Assumming that the grey values of the pixels are "1" for a hole and "0" for a solid area, then the total grey values of the complete convolution windows can be tabulated as shown in FIG. 11. Assuming "4" to be the average peak value then it is immediately apparent where there are defective apertures and whether they are too small (aperture 106) or too big (aperture 108). This can be confirmed by representing graphically the convoluted grey values relating to each row of the tabular summary. By way of example FIGS. 12A, 12B and 12C illustrate rows 1, 3 and 9, respectively, of the tabular summary shown in FIG. 11.

By a suitable adaption of the convolution card 46, for example to include more line stores which are selectable and a preselectable end column subtractor 82, and of the error detection card 48 then the size of the convolution window can be adaptable electronically to any one of a number of predetermined sizes. This is necessary because of the different sizes of shadow masks being etched and the requirement to inspect them using the same fixed apparatus. If desired, coding such as bar coding can be used to identify each size of shadow mask and by reading the bar codes the fixed apparatus can adapt itself as required.

Storing the grey values of individual pixels also enables a diagnosis to be made for particular types of error. For example a defect such as excessive width, apertures 18 and 24 in FIG. 2 or aperture 108 in FIG. 10, can be determined by having a second convolution card producing say a 1 pixel long by 3 pixel wide convolution window. Thus by examining the horizontal row 11 in FIG. 10 and having a 1×3 convolution window then the sums of the grey level values as this window is moved from left to right are as follows: 0, 0, 1, 1, 1, 0, 0, 1, 2, 2, 1, 0, 1, 1, 1, 0, 0, 1, 1, 1, 0, 0. Knowing the row and column coordinates it is possible to determine the location of the defective aperture and to which side of the nominal aperture position the defect lies.

This first embodiment functions satisfactorily, but with suitable modifications to the electronic hardware and to the signal processing in the modified electronic hardware, a better measurement of an aperture shape and the transmission of an aperture can be made. In the first embodiment the threshold values against which the peak value of a currently measured aperture is compared are determined by averaging the peak values of the preceding n apertures where n equals 4, 8, 16 or 32. However a more accurate comparison can be made if the threshold values are based on the average of the peak values of apertures in the immediate vicinity of the currently measured aperture. By the immediate vicinity is meant either the peak values of apertures immediately preceding and immediately following the currently measured aperture in the scanning direction or the peak values of those apertures around the currently measured aperture. In either case extra storage is necessary to build-up a short term history of the peak values which can be read-out in the desired sequence, averaged to provide the required threshold values against which the stored peak value of the currently measured aperture can be compared.

Another critical aspect of the first embodiment of the present invention is that in order to obtain a good result the mechanical construction of the apparatus must be very precise in order to obtain accurate contiguous line scanning by the laser beam. In particular there has to be good coordination between the feed rate of the mask sheet material through the inspection area and the rate of rotation of the scanning prism 60.

This mechanical specification can be relaxed by using a larger spot of radiant energy which itself can have a lower resolution but at the same time the transmission of a mask aperture can still be determined accurately. Alternatively, other methods of scanning can be adopted. The choice of scanning method can depend on a number of factors one of which is the number of additional measurements it is desired to make besides the basic one already described.

Figure 13:
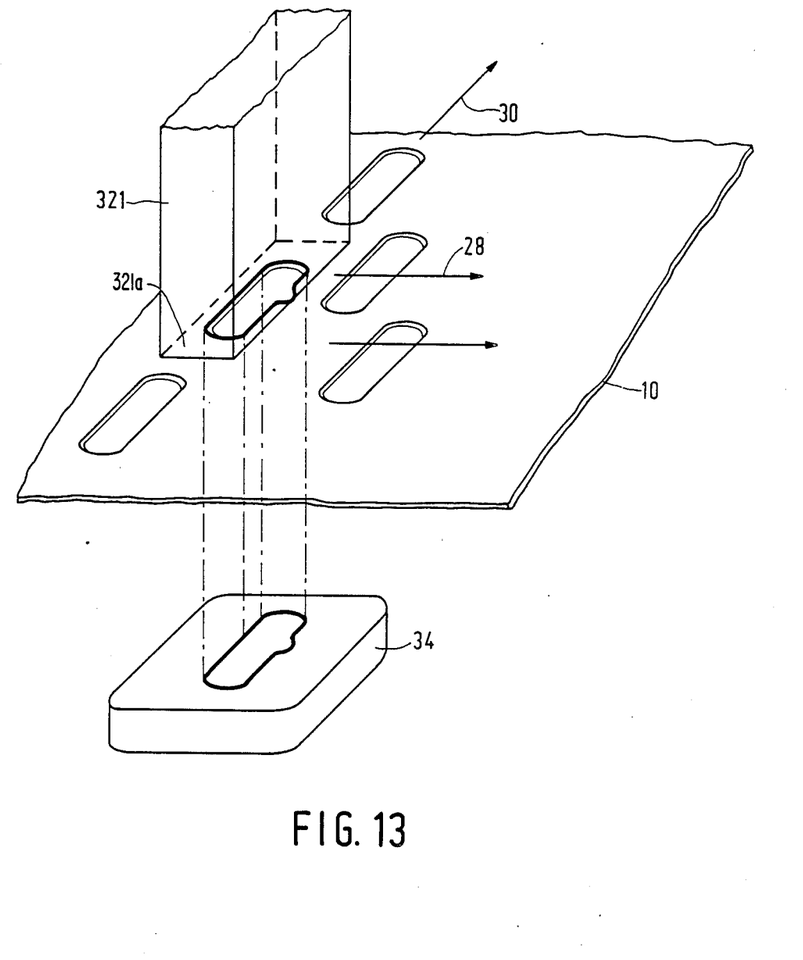
FIG. 13 illustrates diagrammatically another embodiment of the present invention in which the scanning of the mask sheet and the convolution of the data is done using a large spot of radiant energy.

FIG. 13 illustrates the principle of a second embodiment of the method in accordance with the present invention. In this embodiment the size of the laser spot 321a is equivalent to the convolution window, say 3×5 pixels, so that the detected grey level may be regarded as an optical convolution level of pixel sized areas. The beam 321 is scanned linearly across the mask sheet 10 and the total grey value of the laser light passed by the mask sheet is detected at 1 pixel intervals. As the spot 321a has already convoluted the grey level data to the values shown for example in the tabular summary of FIG. 11, these values can be applied immediately, without additional electronic convolution, to the EDC 48.

This second embodiment has the advantage that it avoids the need for the CVC 46 but this is at the expense of flexibility in adapting the method rapidly to different mask sizes and to measuring a range of specific types of defects in a mask simultaneously. Although the size of the spot 321 can be adjusted optically to different mask sizes, it is not regarded as being convenient.

Figure 14:
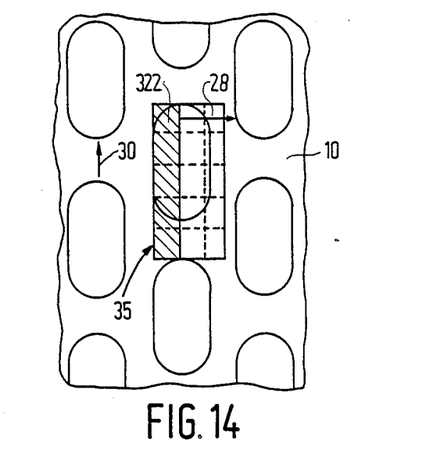
FIG. 14 illustrates diagrammatically a further embodiment of the present invention in which the scanning of the mask sheet is done using an elongate spot of radiant energy.

FIG. 14 illustrates the principle of a third embodiment of the method in accordance with the present invention, which embodiment may be regarded as falling between the first and second embodiments because as will be described, convoluting the grey level values will be done partly by having a larger spot than was used in the first embodiment and partly by electronic processing. In the third embodiment the spot 322 is elongate, having a length equal to the nominal length of an aperture plus the height of a bridge between successive apertures, say, spot length of 5 pixels, and a width equal to one pixel. Thus in the case of a 3 pixel ×5 pixel convolution window then three successive digitised grey levels have to be summed. The scanning of the mask sheet 10 by the elongate spot 322 in the direction 28 is linear, with each succeeding scan being displaced by one pixel length from the preceding linear scan as a consequence of the movement of the mask sheet in the direction 30.

The signal processing generally resembles that described previously with reference to FIGS. 6 to 9, the main difference occurring in the CVC46. Comparing the CVC46 shown in FIG. 15 with that shown in FIG. 7, the main difference is that there are no line stores.

Figure 15:
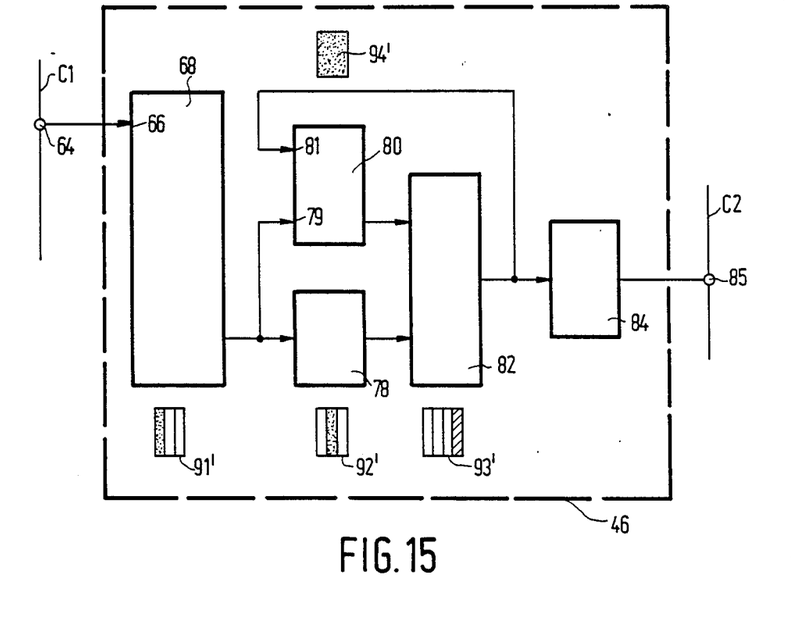
FIG. 15 is a block schematic diagram of a convolution card for use with the embodiment of FIG. 14, FIGS. 16 and 17 are diagrammatic illustrations of embodiments in which the scanning of the mask sheet is carried out by the radiant energy detector.

In FIG. 15 the digitised grey level signal derived from the detected mask transmission of the 1 pixel ×5 pixel scanning laser spot and processed in the LAU44 (FIGS. 5 and 6) is applied to the channel C1. This signal information is applied in sequence to the input 66 of the column adder 68, see pictogram 91'. At the next instant or clock pulse, this digitised grey level signal is transferred to the column shifter 78, see pictogram 92', and also to the input 79 of the area adder 80. The next following grey level signal on the channel C1 is then applied to the column adder 68. When three successive digitised grey level signals have been added then the output of the area adder 80 is equal to the grey level of the 3 pixel ×5 pixel convolution window pictogram 94'. At the occurrence of the transfer of the fourth digitised grey level signal from the column adder 68 to the area adder 80 it is added to the currently held sum value. In the meantime the column shifter 78 has transferred the longest held signal to the end column subtractor 82, pictogram 93'. The subtractor 82 subtracts the digital value of the longest held signal from the new sum signal on the output of the area 80 and provides an output signal which corresponds to the grey level of a convolution window constituted by the 2nd, 3rd and 4th grey level signals. This output is stored in the area adder 80 via its input 81 and is also normalised to eight bits in the normalisation block 84 and thereafter is applied to the channel C2. The signal processing subsequently proceeds as has been described already with reference to FIGS. 8 and 9 and in the interests of brevity it will not be repeated.

In the three embodiments described so far the linear scanning is implemented by moving a beam of radiant energy, for example laser light, across the etched sheet metal 10 and directing the light transmitted onto the detector 34 (FIGS. 3, 6 and 13). However, other methods of scanning include uniformly illuminating the mask sheet 10 by an elongate light source 112 (FIG. 16) and detecting the light transmitted by a scanning detector such as a television camera 114 (FIG. 16) positioned to linearly scan the other side of the mask sheet 10. Another example of a scanning detector is shown diagrammatically in FIG. 17 and comprises a linear array 116 of say up to two thousand photosensitive diodes which are sequentially scanned for example by the electronic equivalent of the rotary switch 118.

Figure 16:
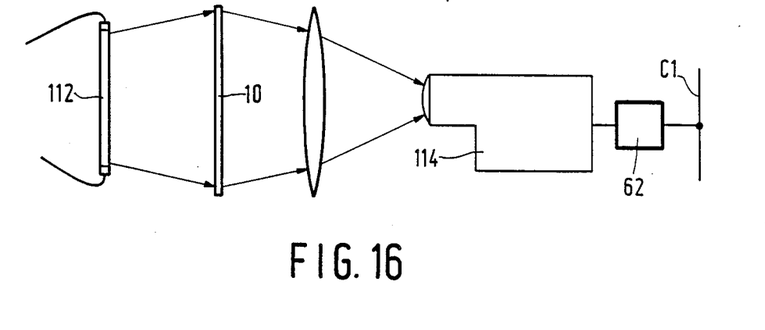
Figure 17:
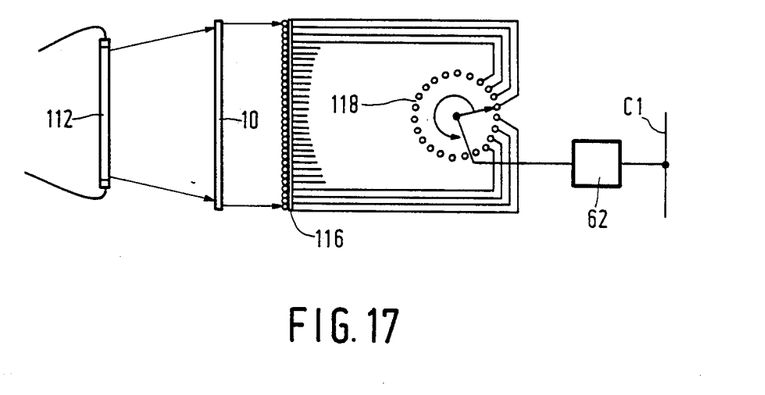

When using the television camera 114 the size of a pixel is determined by the clocking of the A/D converter 62 which digitises the analogue grey level signal. When using the linear array 116 of photosensitive diodes, the pixel size is determined by the pitch of the photo-sensitive diodes.

Another embodiment of the method in accordance with the present invention which enables the method to be applied to situations where the mask pitch varies and/or the size of the spot of radiant energy is equal to or greater than an arbitrary minimum size, comprises processing the digitised grey levels as described before to obtain normalised convoluted values on the channel C2. The series of peak values obtained are divided into two sub-series, a first of the sub-series comprising the even numbered peaks and a second of sub-series comprising the odd numbered peaks. The first and second sub-series are then applied to respective error detection cards. Each error detection card derives its own threshold values on the basis of averaging say the preceding n peak values, where n=4, 8, 16 or 32. The forming of the sub-series and separate processing of them has been found to provide an accurate result even though the size of the spot of radiant energy has not been optimised to suit the different mask sizes being etched.

Figure 18:
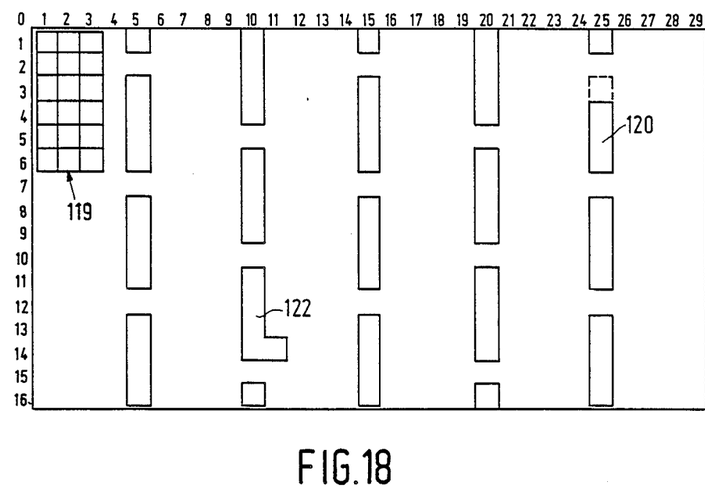
FIGS. 18 and 19 illustrate diagrammatically another simplified numerical example in which alternate peak values are compared with a respective reference value to obtain an accurate assessment of a hole shape and its transmission.
Figure 19:
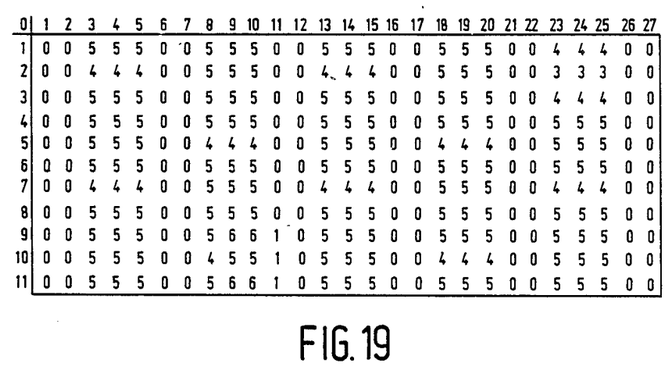

In order to illustrate this technique in a simple way, if the mask sheet of FIG. 18 is scanned using an oversized 3 pixel ×6 pixel spot 19 of radiant energy, then the tabulated grey levels shown in FIG. 19 would be obtained. An inspection of the tabular summary of FIG. 19 indicates that with the correctly shaped holes, then in any one line, for example line 5, 6 or 7, the even numbered peaks are of equal value and the odd numbered peaks are of equal value although as illustrated in line 5 the even equal value is different from the odd value. The tabular summary also illustrates that defective apertures can still be detected by this technique. In the case of aperture 120 (FIG. 18), column positions 23, 24 and 25 of rows 1 to 3 indicate an error if a comparison is made with column positions 2, 3 and 4 and 13, 14 and 15 in the same rows. Similarly in the case of the aperture 122 (FIG. 18), column positions 8 to 10 in rows 9, 10 and 11 of the tabular summary of FIG. 19 indicate an error if a comparison is made with column positions 18 to 20 in the same rows.

Another quality control check which is frequently carried out when manufacturing shadow masks is the transmission of the mask sheets. It is known to do this manually by selecting mask sheets at random and measuring the transmissions at statistically predetermined points on the mask sheets. From these measurements the transmission is calculated. This type of estimation of the mask transmission can be superseded by simply storing all the digitised peak values in a frame store and either summing them or selectively interrogating the stored peak values in order to obtain transmission data in respect of different areas of the etched mask sheet.

What is claimed is:

1. A method of inspecting an apertured mask sheet, characterized by providing relative movement between an apertured mask sheet and a source of radiant energy along a path of movement; producing, by scanning across the mask sheet in a direction transverse to said path of movement, a grey level signal corresponding to radiant energy passed by apertures in the mask sheet; deriving from the grey level signal a plurality of peak signals which correspond to the maximum transmission of each of the apertures scanned; and successively comparing the peak signals with at least one reference value to determine whether the transmission of each aperture scanned is acceptable.

2. A method as claimed in claim 1, wherein the scanning of the mask sheet comprises linearly scanning one side of the mask sheet with a beam of radiant energy and detecting on the other side of the mask sheet the grey level of the radiant energy passed by the apertures in the mask sheet.

3. A method as claimed in claim 2, wherein the beam of radiant energy produces a spot of the order of a picture element (pixel) size, the area of the spot being a predetermined fraction of the area of an aperture in the mask sheet.

4. A method as claimed in claim 3, wherein the detected grey level signals are convoluted by combining electronically the grey levels of successive predetermined arrays of picture elements so that the convoluted data is representative of the overall grey level of respective predetermined areas of the mask sheet, which areas are a fractional area of the mask sheet.

5. A method as claimed in claim 4, wherein the number of pixels in an array can be varied electronically.

6. A method as claimed in claim 4, wherein a second set of convoluted data is produced by electronically combining the grey levels of another predetermined array of pixels.

7. A method as claimed in claim 4, wherein the reference value is formed by averaging the peak values of a predetermined number of convoluted data.

8. A method as claimed in claim 4, wherein the reference value is formed by averaging the peak values of a predetermined number of convoluted data preceding the peak grey level being compared.

9. A method as claimed in claim 4, wherein the reference value is formed by averaging the peak values of a predetermined number of convoluted data preceding and following in time the peak grey level being compared.

10. A method as claimed in claim 4, wherein the reference value is formed by averaging the peak values of a predetermined number of convoluted data spatially surrounding the peak grey level being compared.

11. A method as claimed in claim 2, wherein the beam of radiant energy produces an elongate spot having a length corresponding to substantially the nominal length of an aperture in the mask sheet plus the nominal length of a bridge between two successive apertures and a width which is less than the nominal width of an aperture in the mask sheet.

12. A method as claimed in claim 2 wherein the beam of radiant energy comprises a laser beam.

13. A method as claimed in claim 1, wherein the scanning of the mask sheet comprises substantially evenly illuminating one side of the mask sheet and on the other side of the mask sheet substantially linearly scanning the detected radiant energy passed by the apertures.

14. A method as claimed in claim 13, wherein the linear scanning of the detected radiant energy is effected by a television camera.

15. A method as claimed in claim 13, wherein the linear scanning of the detected radiant energy is by sequentially clocking the outputs produced by a linear array of photosensitive diodes.

16. A method as claimed in claim 1, wherein the beam of radiant energy produces a spot having a size greater than that of the nominal size of an aperture in the mask sheet, and wherein each of the detected grey level signals represents a convolution of the grey levels occurring in a plurality of picture element (or pixel) sized areas, said areas having a size corresponding to a sub-multiple of the area of an aperture.

17. A method as claimed in claim 16, wherein the detection of the grey level of the spot is determined at time intervals corresponding a sub-multiple of the time of travel of the spot across one aperture of the mask sheet.

18. A method as claimed in claim 16, wherein the spot has a length corresponding to the nominal length of a mask aperture plus the height of a bridge between successive apertures and a width greater than the nominal maximum width of an aperture.

19. A method as claimed in claim 16, wherein the beam of radiant energy comprises a laser beam.

20. A method as claimed in claim 1, wherein alternate ones of the sequentially derived peak signals are formed respective sub-sequences, and wherein the peak values in each sub-sequences are compared with a respective reference value.

21. A method as claimed in claim 1, wherein the reference value is adaptive.

22. A method as claimed in claim 1, further comprising storing all the peak values and determining the overall mask transmission from the stored values.

23. A method as claimed in claim 1, wherein the mask sheet is moving continuously along its path of movement.

24. Apparatus for inspecting an apertured mask sheet, comprising radiant energy producing means and radiant energy detecting means for detecting the amount (or grey level) of radiant energy passed by the mask sheet disposed on opposite sides of a path of relative movement of the mask sheet, said producing means and detecting means being so constructed and operated that a linear scan, transverse to said path of movement, can be effected, means for deriving a succession of peak signals which correspond to the maximum transmission of each of the apertures scanned from the detected grey levels, and comparing means for comparing each peak signal with at least one reference value.

25. An apparatus as claimed in claim 24, wherein the radiant energy producing means comprises a scannable light source and means are provided for directing the radiant energy passed by the mask sheet apertures onto said detecting means.

26. An apparatus as claimed in claim 25, wherein the scannable light source comprises a laser scanner.

27. An apparatus as claimed in claim 24, wherein the radiant energy producing means comprises means for illuminating substantially evenly one side of the mask sheet and the detecting means is constructed to linearly scan the radiant energy passed by the mask sheet.

28. An apparatus as claimed in claim 24, further comprising means for digitising the analogue values of the detected grey level signals and means for convoluting the digitised grey level signals so that each convoluted signal is representative of the grey level of the radiant energy passed by a predetermined area of the mask sheet.

29. An apparatus as claimed in claim 24, further comprising means for producing at least one reference value by forming an average of a predetermined number of peak signals.

30. An apparatus as claimed in claim 24, wherein said comparing means comprises means for forming two sub-sequences from alternate ones of the succession of peak signals and means for comparing the peak values in each sub-sequence with a respective reference value.

31. An apparatus as claimed in claim 24, further comprising means for storing the peak signals and providing an output indicative of the transmission of the mask sheet.

* * * * *